United States Patent [19]
Gough et al.

[11] Patent Number: 5,837,127
[45] Date of Patent: Nov. 17, 1998

[54] PROCESS FOR CRACKING AND TRANSHYDROGENATION OF HYDROCARBON FEEDSTOCK

[75] Inventors: Arthur Gough, North Yorkshire; Stephen Keith Turner, Cleveland; Jane Mercer; Edmund Hugh Stitt, both of Cleveland, all of United Kingdom

[73] Assignee: Institut Francais du Petrole, France

[21] Appl. No.: 407,019

[22] PCT Filed: Oct. 15, 1993

[86] PCT No.: PCT/GB93/02136

§ 371 Date: Jun. 23, 1995

§ 102(e) Date: Jun. 23, 1995

[87] PCT Pub. No.: WO94/10264

PCT Pub. Date: May 11, 1994

[30] Foreign Application Priority Data

Oct. 26, 1992 [GB] United Kingdom ................... 9222416

[51] Int. Cl.$^6$ .................................... C10G 69/02
[52] U.S. Cl. ............................ 208/60; 585/257; 585/616; 585/627; 585/661; 585/660
[58] Field of Search ..................... 585/257, 661, 585/660, 616, 627; 208/60

[56] References Cited

U.S. PATENT DOCUMENTS

| | | |
|---|---|---|
| 2,322,025 | 6/1943 | Ipalieff et al. ........................... 585/257 |
| 3,211,635 | 10/1965 | Phillips Petroleum . |
| 3,267,170 | 8/1966 | Aldridge et al. ......................... 585/257 |
| 3,267,171 | 8/1966 | Esso ..................................... 260/683.3 |
| 3,321,545 | 5/1967 | Rigney et al. ........................... 585/257 |
| 3,855,327 | 12/1974 | Billings ................................... 585/257 |
| 3,950,447 | 4/1976 | Gryaznov ................................. 585/257 |
| 4,062,803 | 12/1977 | Bianchi et al. ......................... 585/257 |
| 4,546,204 | 10/1985 | Parris ...................................... 585/257 |
| 4,684,755 | 8/1987 | Parris et al. ............................. 525/257 |
| 4,975,097 | 12/1990 | Harandi et al. ......................... 585/257 |
| 5,047,070 | 9/1991 | Harandi et al. ......................... 585/324 |
| 5,160,424 | 11/1992 | Le et al. .................................... 208/60 |
| 5,585,530 | 12/1996 | Gough ..................................... 585/257 |
| 5,639,926 | 6/1997 | Turner et al. ........................... 585/259 |

FOREIGN PATENT DOCUMENTS

| | | | |
|---|---|---|---|
| A 0 221 332 | 5/1987 | Australia ........................ C07C 5/52 |
| WO A 92 19575 | 11/1992 | Australia . |

*Primary Examiner*—Helane Myers
*Attorney, Agent, or Firm*—Millen, White, Zelano & Branigan, P.C.

[57] ABSTRACT

A hydrocarbon feedstock is cracked, and then the cracker product is compressed and separated into various hydrocarbon fractions including a stream containing hydrocarbons more highly unsaturated than mono-olefins. That stream is used for transhydrogenation with at least one paraffin and the products from transhydrogenation are combined with the cracker product before the compression thereof.

11 Claims, 2 Drawing Sheets

/ 5,837,127 /

PROCESS FOR CRACKING AND TRANSHYDROGENATION OF HYDROCARBON FEEDSTOCK

BACKGROUND OF THE INVENTION

This invention relates to hydrocarbons and in particular to the production of olefins, or derivatives thereof, from a hydrocarbon feedstock stream.

It is well known that a hydrocarbon feedstock stream, such as naphtha, LPG, or gas-oil, may be cracked in a furnace to give a mixture of hydrocarbons of varying molecular weight. Often the aim of such a cracking operation is to produce olefins containing up to about 5 carbon atoms, although inevitably non-olefinic compounds and also some higher molecular weight products will usually be formed. The cracking process gives a mixture of hydrogen and saturated, unsaturated, and aromatic hydrocarbons. The precise composition of the cracker product will of course depend on the nature of the feedstock and the cracking furnace operating conditions; a typical percentage composition (by weight) of the product of cracking naphtha is as follows:

| hydrogen | 1 | benzene | 6 |
|---|---|---|---|
| methane | 16 | toluene | 3 |
| ethene | 32 | $C_8$ aromatics | 2 |
| propene | 16 | fuel oil | 4 |
| $C_4$ hydrocarbons | 8 | others | 12 |

The cracker product is usually separated, e.g., by distillation, into a number of streams, such as hydrogen, methane, $C_2$, $C_3$, $C_4$, and higher hydrocarbon streams. Usually it is desired to produce olefin streams and to this end the $C_2$, $C_3$ and/or the $C_4$ streams are separated into the appropriate olefinic and paraffinic streams. Often the paraffinic streams are recycled to the cracking furnace. The cracking operation is normally effected at temperatures in the range 750°–900° C., particularly 800°–850° C., using steam as a diluent, usually in proportions of 0.25–0.75, particularly 0.4–0.6, tonnes of steam per tonne of hydrocarbon feedstock. The cracking is usually non-catalytic and is effected at relatively low pressure, generally below about 10 bar abs. and often below about 2 bar abs. The cracker product, possibly after an initial separation of at least some of the hydrocarbons containing 5, 6, or more carbon atoms, is then compressed, typically to above about 20 bar abs., before effecting the separation into the desired product streams by means of a suitable cold train and separation columns.

The olefin components are generally the highest value products and so it is often desirable to increase the yield of such components. Also among the cracker products are components, such as propadiene, propyne, and butadiene, that are more highly unsaturated than mono-olefins. In PCT application GB92/00699 (now published as WO 92/19575) —the disclosure of which is incorporated herein by reference—a process termed transhydrogenation is described wherein such more highly unsaturated hydrocarbons are catalytically reacted with paraffins, effecting dehydrogenation of the paraffins and hydrogenation of the more highly unsaturated components. The paraffins thus act as hydrogen-donors while the more highly unsaturated hydrocarbons act as hydrogen-acceptors.

Such a transhydrogenation process, which like cracking is desirably operated at a relatively low pressure for operating reasons, enables the yield of olefins to be increased. The transhydrogenation is desirably effected in the presence of added hydrogen. In addition to the desired olefins, the transhydrogenation product will contain other components, eg hydrogen, unreacted paraffins, unreacted hydrogen-acceptor compounds, together with products resulting from cracking and/or hydrogenation reactions taking place as well as transhydrogenation. Consequently recovery of the desired olefin components from the transhydrogenation product is also necessary. In the present invention this is effected by means of the product separation facilities employed for the separation of the cracker product into component streams.

SUMMARY OF THE INVENTION

Accordingly the present invention provides a process wherein a hydrocarbon feedstock is subjected to cracking at a first pressure to produce a cracker product, the cracker product is compressed, possibly after preliminary separation of higher molecular weight components, to a second pressure greater than said first pressure, and then the compressed cracker product is separated into a number of components including at least one stream containing one or more hydrocarbons more highly unsaturated than mono-olefins, characterized in that at least part of said at least one stream containing hydrocarbons more highly unsaturated than mono-olefins is subjected to transhydrogenation with at least one paraffin stream at a pressure below said second pressure and the products from said transhydrogenation are combined with said cracker product stream before the compression thereof.

As indicated above, in the transhydrogenation process both hydrogenation of the hydrogen-acceptor and dehydrogenation of the hydrogen-donor occur. Hydrogenation reactions are generally exothermic while dehydrogenation reactions are generally endothermic. By effecting the dehydrogenation of the hydrogen-donor in the presence of the hydrogen-acceptor, at least some of the heat required for the dehydrogenation is in effect provided by hydrogenation of the hydrogen-acceptor. In the present invention, preferably at least 25%, particularly at least 50%, and more particularly at least 70%, of the heat required for dehydrogenation of the hydrogen-donor is in effect provided by the exothermic hydrogenation of the hydrogen-acceptor. As a result, the reaction conditions may be adjusted such that the reaction is net endothermic, net exothermic or thermally neutral: also as indicated above, the transhydrogenation reaction is preferably effected in the presence of hydrogen and the reaction conditions may be such that there is a net production or net consumption of hydrogen. The ability to operate in the presence of hydrogen may be advantageous to decrease the tendency to coke formation.

In the transhydrogenation process, dehydrogenation of the hydrogen-donor takes place: generally the conditions are such that some dehydrogenation thereof would take place even if the hydrogen-acceptor was omitted. The operating conditions, employed, e.g., temperatures and pressures, will depend on the choice of catalyst, the hydrogen partial pressure, and the nature of the hydrogen-donor and hydrogen-acceptor. Preferably the conditions are such that a total of at least 10% by weight of the hydrogen-donor is dehydrogenated.

The total pressure in the transhydrogenation process is preferably in the range 0.3 to 20, particularly 0.5 to 10, and more particularly in the range 1 to 5, bar abs. The partial pressure of hydrogen-donor plus hydrogen-acceptor is preferably in the range 0.1 to 20, particularly 0.1 to 5, bar abs. The temperature is preferably in the range 200° to 800° C., particularly 400° to 700° C.

Although elevated temperatures are required, often necessitating preheating of the reactants, since the process is preferably operated such that at least 25% of the heat required for the dehydrogenation of the hydrogen-donor is supplied by hydrogenation of the hydrogen-acceptor, far less heat input is required than in dehydrogenation in the absence of the hydrogen-acceptor. Thus heat can be recovered from the products and, by feed/effluent heat exchange, used to provide most, if not all, of the heat required to reach the reaction temperature.

The amount of hydrogen-donor is from 0.5 to 20, particularly 1 to 10, and more particularly 2 to 10, moles for each mole of hydrogen-acceptor employed. Preferably the molar amount, if any, of hydrogen added is less than 10 times the total molar amount of hydrocarbon present.

The transhydrogenation reaction may be effected in the presence of a diluent such as steam which, in some cases, may suppress coke formation and/or may serve to activate the catalyst. Methane may alternatively or additionally be used as a diluent.

The hydrogen-acceptor stream may typically comprise dienes and/or acetylenes alone or in admixture with mono-olefins and/or paraffins. Examples of suitable hydrogen-acceptor streams that may be separated from the cracker product and used for transhydrogenation include propyne, propadiene, butadiene-1,2, butadiene-1,3, and mixtures thereof, eg propyne plus propadiene; $C_4$ streams such as a mixed $C_4$ stream; and $C_5$ gasoline, and/or full range pygas streams. It is preferred that the hydrogen-acceptor comprises at least one stream containing $C_3$ and/or $C_4$ hydrocarbons.

The hydrogen-donor is preferably at least one paraffin containing 2 or more carbon atoms, for example ethane, propane, n-butane, 2-methylpropane, mixed $C_4$ paraffins, paraffins containing 5 or more carbon atoms. Alternatively, or additionally, it may comprise ethylbenzene or a similar alkyl aromatic with alkyl groups containing 2 or more carbon atoms. It will be appreciated that the hydrogen-donor stream may contain, in addition to at least one hydrogen-donor compound that is free from olefinic unsaturation, other components such as mono-olefins.

In some cases, by suitable selection of the reaction conditions and/or catalyst, some desired isomerisation of the reactants may accompany the transhydrogenation reaction.

It may be convenient, although not essential, that the hydrogen-acceptor and hydrogen-donor compounds contain the same number of carbon atoms: in this way the olefin produced will also contain the same number of carbon atoms. As examples there may be quoted propane with propyne and/or propadiene; and 2-methyl propane and/or n-butane with butadiene or with a mixed $C_4$ stream containing butadiene.

In a preferred form of the invention, a stream containing $C_3$ hydrocarbons, ie propane, propene, propadiene and/or propyne, is separated from the compressed cracker product, propene is separated from this $C_3$ stream, and at least part of the remainder of this $C_3$ stream, ie containing propane, propyne and/or propadiene, is used as at least part of the one or more streams containing one or more highly unsaturated hydrocarbons and/or as at least part of the paraffin stream subjected to transhydrogenation.

The transhydrogenation process is effected in the presence of a dehydrogenation catalyst. By the term dehydrogenation catalyst we mean a catalyst that will effect dehydrogenation of the hydrogen-donor under the conditions employed. The catalyst employed will depend on the nature of the hydrogen-acceptor and hydrogen-donor compounds. Suitable catalysts include noble metals, eg platinum and/or other platinum group metals such as palladium, on a support such as alumina; such catalysts modified with other species, eg Group IV elements such as tin; chromia, alone or in conjunction with a platinum group metal or iron oxide, on a support such as alumina, zirconia and/or alkaline earth oxides, especially those stabilised for use at high temperatures; platinum group metals supported on such supports. Sulphided versions of the above catalysts and/or molybdenum sulphide may also be used. However, unless the reaction is effected in the presence of added hydrogen and/or the catalyst is sulphided or otherwise moderated, platinum on alumina may not be suitable for some processes as some polyunsaturated compounds, eg butadiene, may be so strongly adsorbed that there is negligible reaction with the hydrogen-donor, eg paraffin. Chromia, optionally in admixture with a platinum group metal, and preferably doped with alkali, on alumina is particularly suitable. Another particularly suitable catalyst is a mixture of platinum and tin, supported on alumina, again preferably doped with alkali. In alkali doped catalysts, the alkali is preferably potassium or cesium.

Where the transhydrogenation process conditions are such that coke is deposited on the catalyst, the catalyst may be regenerated periodically by passing hot air, optionally mixed with nitrogen, over the catalyst. Other regeneration processes known in the dehydrogenation art, using eg steam and/or hydrogen, may be employed. In some cases it may be desirable to employ two or more transhydrogenation units so that while one or more units is on-line the other unit or units are undergoing regeneration. Alternatively a moving catalyst bed type of reactor may be employed.

Adjustment of the five main transhydrogenation reaction variables, viz total pressure, temperature, residence time, hydrogen-donor/hydrogen-acceptor ratio, and hydrogen partial pressure, enables control to be exercised over the transhydrogenation product composition and can determine whether the reaction is a net generator or consumer of hydrogen or is a net generator or consumer of heat.

In the process of the invention at least some of the hydrogen-donor fed to the transhydrogenation stage may be a paraffin stream separated from the cracking furnace product stream. Preferably an additional feed of a suitable paraffin stream is also employed. The paraffin stream used in the transhydrogenation preferably contains propane and/or 2-methyl propane.

Where a $C_4$ stream is employed to provide a hydrogen-acceptor stream, it is generally desirable, prior to such use, to subject the $C_4$ stream separated from the cracking furnace product to a further separation step to give a stream enriched in butadiene. This butadiene-enriched $C_4$ stream is employed as the hydrogen-acceptor stream, while some or all of the remainder may be recycled to the cracking furnace. Since complete separation is not here required, the usual difficulties in separation of $C_4$ hydrocarbons are not here a problem. A pressure swing adsorption method may be employed to effect this separation. It is however preferred that the separation is such that the $C_4$ hydrocarbons stream remaining after separation of the butadiene-enriched stream contains at least some of the butenes present in the $C_4$ stream separated from the compressed cracker product.

In some cases it may be desired to produce an olefin derivative as a primary product. An example of such a product is methyl t-butyl ether (MTBE) which can be synthesised, as is well known in the art, from 2-methyl propene and methanol. Such a synthesis step may be employed as a method of effecting the separation of the desired olefin from the cracker product. For example a $C_4$ stream separated, eg by distillation, from the cracker product may be reacted with methanol, and MTBE formed by reaction of the 2-methyl propene in the $C_4$ stream separated, leaving a $C_4$ stream depleted in 2-methyl propene. This stream, which will contain butadiene, may be used as the hydrogen-acceptor stream. Preferably the stream depleted in 2-methyl propene is subjected to a further separation step, as aforesaid, to produce a stream enriched in butadiene for use as at least part of the hydrogen acceptor stream and a stream containing at least some of the remaining butenes, as well as butanes. This stream containing butenes and butanes may be recycled to the cracking furnace.

In the process of the invention, by employing the same compressor and separation stages for the treatment of both the cracker product and the transhydrogenation product, duplication of equipment is minimized.

BRIEF DESCRIPTION OF THE DRAWINGS

Two embodiments of the invention will now be described with reference to the accompanying drawings wherein.

DETAILED DESCRIPTION OF THE DRAWINGS

Figure 1:
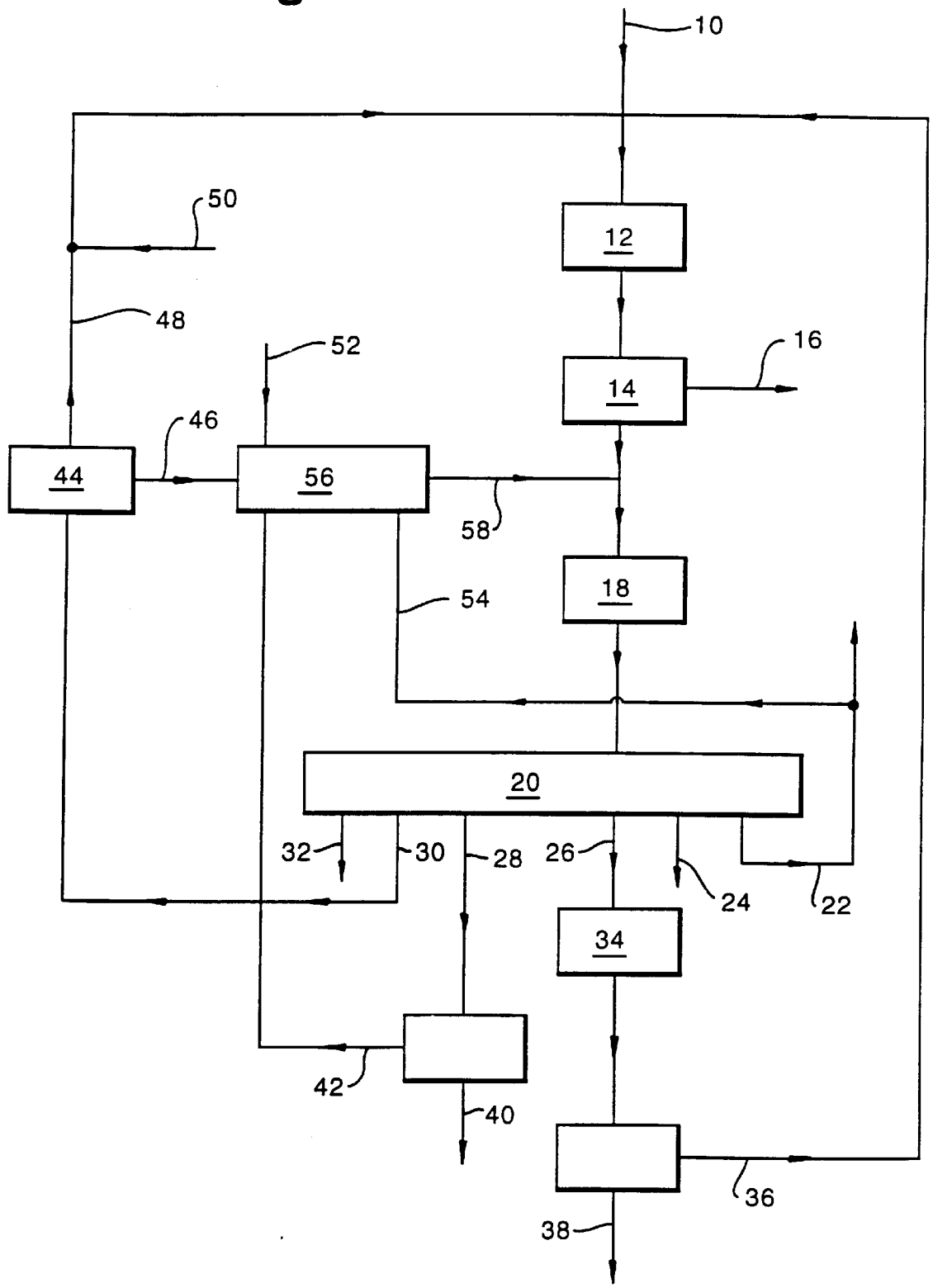
FIG. 1 is a diagrammatic flowsheet of a process wherein the desired primary products are ethene and propene.

In the process of FIG. 1 a naphtha feedstock stream 10 is fed to a cracking furnace 12 together with steam (not shown) wherein the feedstock is cracked, typically at about 840° C. and substantially at atmospheric pressure. Optionally recycled ethane and/or recycled butanes and/or imported propane and/or imported butane, can be added to the naphtha stream prior to feeding to the cracking furnace. The cracker product is then cooled and passed to a primary fractionator 14 wherein the bulk of the hydrocarbons containing 5 or more carbon atoms are separated as one or more streams 16 for further processing. The remaining cracker product is then compressed by compressor 18, typically to about 35 bar abs., and fed to a conventional cold train and separation unit 20. Although shown as a single unit, it will be appreciated that the separation unit 20 may comprise a series of stages. The separation unit 20 effects separation of the compressed cracker product into a number of streams, typically a hydrogen stream 22, a methane stream 24, a $C_2$ stream 26, a $C_3$ stream 28, a $C_4$ stream 30, and a higher hydrocarbon stream 32.

As is well known, the $C_2$ stream may be subjected to selective hydrogenation in a selective hydrogenation unit 34, to convert any ethyne therein to ethene and then separated into an ethane stream 36 and a ethene stream 38 forming a first primary product stream. At least part of the ethane stream 36 may be recycled as shown to the cracking furnace as the aforesaid optional recycle ethane stream.

The $C_3$ stream 28 is normally likewise subjected to selective hydrogenation to convert any propyne or propadiene therein to propene, but in this embodiment of the present invention such a step is not necessary. In the present embodiment of the invention, the $C_3$ stream is separated into a propene stream 40 forming a second primary product stream and a propane stream 42 also containing any propyne and propadiene.

The $C_4$ stream 30 is separated in a $C_4$ splitter 44 into a butadiene-rich stream 46 and a butanes-rich stream 48. Splitter 44 should also effect at least partial separation of butenes in the stream 30 into the butanes-rich stream 48. Unless butanes and/or butenes are required as a further primary product, the butanes-rich stream 48 is recycled as shown to the cracking furnace as the aforesaid recycled butanes stream. Imported butane may be added to this butanes-rich stream 48 via line 50 if desired.

The butadiene-rich stream 46, together with the propane stream 42, an imported propane stream 52, and hydrogen, if desired, taken from stream 22 via line 54, is fed to a transhydrogenation stage 56, typically operating at 500°–600° C. and substantially at atmospheric pressure. Part of the imported propane stream 52 may be fed to the cracking furnace 12 as the aforesaid imported propane stream. In the transhydrogenation stage 56, the propane from streams 42 and 52 is transhydrogenated with the butadiene in stream 46 and the propyne and propadiene in stream 42, over a catalyst such as platinum plus tin on alumina. The transhydrogenation product stream 58 comprising a mixture of hydrogen and hydrocarbons, both saturated and unsaturated and primarily consisting of $C_1$ to $C_4$ hydrocarbons, is added to the cracking furnace product, before or after primary fractionator 14, but before compression in compressor 18. The compressor 18 and the cold train and separation unit 20 serve to effect separation of both the cracker product and the transhydrogenation product.

Figure 2:
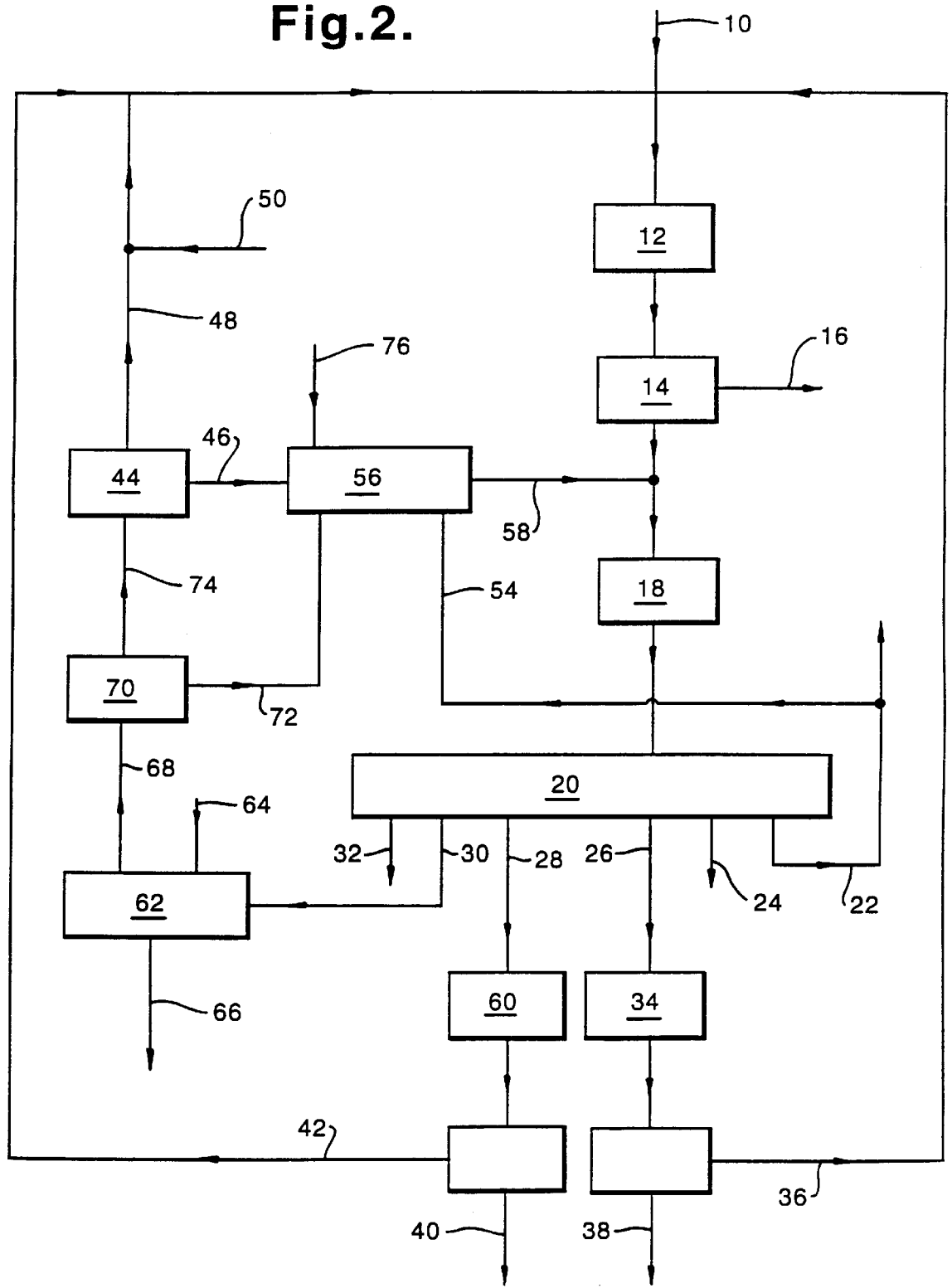
FIG. 2 is a flowsheet similar to FIG. 1 but of a process where MTBE is also a desired primary product.

In the embodiment of FIG. 2, a similar arrangement is employed, but the $C_3$ stream 28 is subjected to selective hydrogenation in unit 60 before splitting into the primary propene product stream 40 and the propane stream 42. Instead of feeding the propane stream 42 to the transhydrogenation stage, it is recycled, unless propane is desired as a further primary product, as part of the feed to the cracking furnace. The $C_4$ stream 30 is fed to a MTBE synthesis and separation stage 62, wherein 2-methyl propene in the $C_4$ stream 30 is reacted with methanol supplied thereto as stream 64 and the synthesised MTBE is separated as stream 66, leaving a $C_4$ stream 68 that is depleted in 2-methyl propene.

Stream 68 is then fed to a first $C_4$ splitter 70, where it is separated into a stream 72 containing primarily 2-methyl propane, some butene-1, and some butadiene, and a stream 74 containing primarily n-butane, together with the remainder of the n-butenes and butadiene. Stream 74 is optionally separated in a second $C_4$ splitter 44 to give a butadiene-rich stream 46 and a n-butane-rich stream 48. Pressure swing adsorption units may be employed for the $C_4$ separations. Stream 48 may be recycled to the cracking furnace as the recycle butane stream, optionally with the addition of n-butane imported as stream 50. Stream 72, together with stream 46 (if the second $C_4$ splitter 44 is employed), 2-methyl propane imported as stream 76, and hydrogen stream 54 are fed to the transhydrogenation stage 56. In this stage, the butadiene in stream 72 (and in stream 46, if used) acts as a hydrogen-acceptor while the 2-methyl propane in stream 72, and that imported as stream 76, acts as a hydrogen-donor producing a stream of hydrocarbons containing an increased proportion of 2-methyl propene. As in the embodiment of FIG. 1, the transhydrogenation product stream 58 is added to the cracker product before or after primary fractionator 14, but before compression in compressor 18. The compressor 18 and the cold train and separation unit 20 serve to effect separation of both the cracking furnace product and the transhydrogenation product.

In a variant of the flowsheet of FIG. 2, if the transhydrogenation catalyst exhibits isomerisation activity, and/or an isomerisation stage is employed before or after the transhydrogenation step as described in our PCT application GB 93/00765, imported n-butane may be fed in place of the imported 2-methyl propane.

As an example, the flow rates of a typical flowsheet in accordance with FIG. 1 are shown in the following table. The transhydrogenation is effected under conditions giving no net consumption of hydrogen producing a transhydrogenation product of the approximate composition (by weight):

| | |
|---|---|
| hydrogen plus methane | <1% |
| ethane | 1% |
| propene | 28% |
| propane | 50% |
| $C_4$'s and higher | 21% |

The butadiene rich stream from the $C_4$ splitter has the approximate composition (by weight):

| | |
|---|---|
| butadiene | 80% |
| butene-1 plus 2-methyl propane | 20% |

| Stream | Description | Flow rate (t/h) |
|---|---|---|
| 10 | Naphtha feedstock | 239 |
| 36 | Recycled ethane | 22 |
| 48 | Recycled butanes rich stream | 26 |
| 50 | n-Butane feed | 2 |
| | Total cracker feed | 289 |
| | Feed to separator 14 | 289 |
| 16 | C5 and higher product | 54 |
| | Remainder from separator 14 | 235 |
| 58 | From transhydrogenation | 63 |
| | To separator train 20 | 298 |
| 22 | Separated hydrogen stream | 4 |
| 24 | Separated C1 product | 46 |
| 36 | Ethane stream for recycle | 22 |
| 38 | Ethene product | 84 |
| 40 | Propene product | 57 |
| 42 | C3 stream to transhydrogenation | 36 |
| 30 | Separated C4 stream | 39 |
| 32 | Separated C5 and higher stream | 10 |
| | Total product from separator train | 298 |
| 46 | Butadiene rich stream | 13 |
| 48 | Butane rich stream for recycle | 26 |
| 30 | Feed to C4 splitter | 39 |
| 42 | C3 stream to transhydrogenation | 36 |
| 46 | Butadiene rich stream | 13 |
| 52 | Propane feed to transhydrogenation | 14 |
| 54 | H2 feed to transhydrogenation | 0 |
| 58 | Transhydrogenation product | 63 |

We claim:

1. A process comprising subjecting a hydrocarbon feedstock to cracking at a first pressure to produce a cracker product, compressing the the cracker product to a second pressure greater than said first pressure, and then separating the compressed cracker product into a number of components including at least one stream containing one or more polyunsaturated hydrocarbons, subjecting at least part of said at least one stream containing polyunsaturated hydrocarbons to transhydrogenation with at least one paraffin stream at a pressure below said second pressure, whereby said polyunsaturated hydrocarbons undergo transhydrogenation with said paraffins, and combining the products from said transhydrogenation with said cracker product stream before the compression thereof.

2. A process according to claim 1 wherein at least some hydrocarbons containing 5 or more carbon atoms are separated from the cracker product before the compression thereof.

3. A process according to claim 1, wherein the at least one stream containing one or more highly unsaturated hydrocarbons subjected to transhydrogenation comprises $C_3$ and/or $C_4$ hydrocarbons, whereby said $C_3$ and/or $C_4$ hydrocarbons are transhydrogenated with said paraffins.

4. A process according to claim 1, wherein a $C_3$ stream containing propene in addition to other $C_3$ hydrocarbons is separated from the compressed cracker product, propene is separated from said $C_3$ stream, and at least part of the remainder of said $C_3$ stream is used as at least part of the feed to transhydrogenation, whereby said $C_3$ stream is transhydrogenated with said paraffins.

5. A process according to claim 3 wherein a $C_4$ stream containing butadiene in addition to other $C_4$ hydrocarbons is separated from the compressed cracker product, a stream enriched in butadiene is separated from the $C_4$ stream and subjected to transhydrogenation, whereby said butadiene is transhydrogenated with said paraffins.

6. A process according to claim 5 wherein the stream containing $C_4$ hydrocarbons remaining after separation of said stream enriched in butadiene contains at least some of the butenes present in the $C_4$ stream separated from the compressed cracker product.

7. A process according to claim 5 or claim 6 wherein 2-methyl propene is separated from the stream containing $C_4$ hydrocarbons separated from the compressed cracker product, to produce a 2-methyl propene depleted $C_4$ stream, and then the stream enriched in butadiene is separated from at least part of the 2-methyl propene depleted $C_4$ stream.

8. A process according to claim 7 wherein the 2-methyl propene is separated from the stream containing $C_4$ hydrocarbons by addition of methanol and reaction to produce methyl t-butyl ether.

9. A process according to claim 5 wherein at least part of the $C_4$ stream remaining after separation of the stream enriched in butadiene is recycled to the cracker.

10. A process according to claim 5 wherein at least part of the paraffin stream subjected to transhydrogenation comprises propane and/or 2-methyl propane.

11. A process according to claim 1, wherein said stream containing polyunsaturated hydrocarbons is essentially free of $C_2$-hydrocarbons.

* * * * *